United States Patent
Joyce et al.

(10) Patent No.: US 7,361,156 B2
(45) Date of Patent: Apr. 22, 2008

(54) PRESSURE JACKET SYSTEM WITH PIVOTAL LOCKING MEMBERS

(75) Inventors: Thomas P. Joyce, Wilkins Township, PA (US); Ralph H. Schriver, Tarentum, PA (US); Michael A. Spohn, Butler, PA (US); Salvatore J. Dedola, New Kensington, PA (US)

(73) Assignee: MEDRAD, Inc., Indianola, PA (US)

( * ) Notice: Subject to any disclaimer, the term of this patent is extended or adjusted under 35 U.S.C. 154(b) by 491 days.

(21) Appl. No.: 10/326,583

(22) Filed: Dec. 20, 2002

(65) Prior Publication Data

US 2004/0122370 A1   Jun. 24, 2004

(51) Int. Cl.
*A61M 37/00* (2006.01)

(52) U.S. Cl. .................................... 604/131

(58) Field of Classification Search ............... 604/131, 604/187, 234, 151–4; 128/DIG. 1, 12–3, 128/DIG. 6; 600/432
See application file for complete search history.

(56) References Cited

U.S. PATENT DOCUMENTS

| | | | |
|---|---|---|---|
| 2,702,547 A | 2/1955 | Glass | |
| 3,623,474 A | 11/1971 | Heilman et al. | |
| 4,243,031 A | 1/1981 | Genese | |
| 4,351,332 A | 9/1982 | Whitney et al. | |
| 4,677,980 A | 7/1987 | Reilly et al. | |
| 4,858,127 A | 8/1989 | Kron et al. | |
| 4,966,601 A * | 10/1990 | Draenert | 606/92 |
| 5,002,528 A | 3/1991 | Palestrant | |
| 5,300,031 A * | 4/1994 | Neer et al. | 604/154 |
| 5,383,858 A | 1/1995 | Reilly et al. | |
| 5,460,609 A | 10/1995 | O'Donnell | |
| 5,515,851 A | 5/1996 | Goldstein | |
| 5,520,653 A * | 5/1996 | Reilly et al. | 604/152 |
| 5,569,208 A | 10/1996 | Woelpper et al. | |
| 5,573,515 A | 11/1996 | Wilson et al. | |
| 5,779,675 A * | 7/1998 | Reilly et al. | 604/131 |
| 5,800,397 A | 9/1998 | Wilson et al. | |
| 5,840,026 A | 11/1998 | Uber, III et al. | |
| 5,873,861 A | 2/1999 | Hitchins et al. | |
| 5,916,165 A | 6/1999 | Duchon et al. | |
| 5,947,935 A | 9/1999 | Rhinehart et al. | |
| 6,096,011 A | 8/2000 | Trombley, III et al. | |
| 6,221,045 B1 | 4/2001 | Duchon et al. | |
| 6,241,708 B1 | 6/2001 | Reilly et al. | |
| 6,336,913 B1 | 1/2002 | Spohn et al. | |
| 6,368,307 B1 * | 4/2002 | Ziemba et al. | 604/218 |

(Continued)

FOREIGN PATENT DOCUMENTS

| | | |
|---|---|---|
| WO | WO 97/07841 | 3/1997 |
| WO | WO 00/10629 | 3/2000 |
| WO | WO 02/04049 | 1/2002 |

*Primary Examiner*—Kevin C. Sirmons
(74) *Attorney, Agent, or Firm*—Gregory Bradley; Christian Schuster

(57) ABSTRACT

The fluid injection apparatus for use with the syringe includes an injector and a pressure jacket assembly associated with the injector. The injector includes a housing defining a central opening and a drive piston extendable through the central opening for imparting motive forces to a syringe plunger disposed within the syringe. The pressure jacket assembly includes a pressure jacket and at least one locking member pivotally associated with the pressure jacket. The at least one locking member is movable between an engaged position preventing removal of the syringe from the pressure jacket and a disengaged position allowing insertion and removal of the syringe into the pressure jacket.

12 Claims, 11 Drawing Sheets

U.S. PATENT DOCUMENTS 6,471,674 B1    10/2002   Emig et al.
6,808,513 B2 *  10/2004   Reilly et al. ................ 604/218

2004/0122370 A1   6/2004   Joyce et al.

* cited by examiner

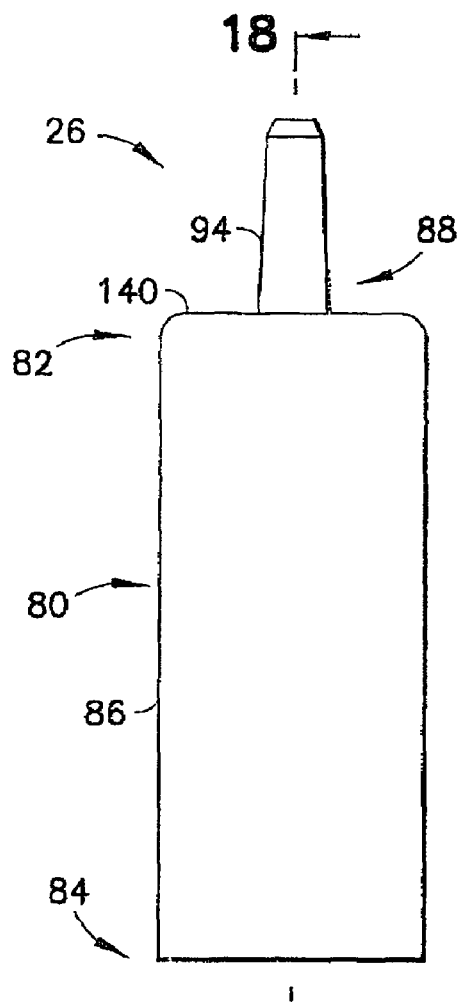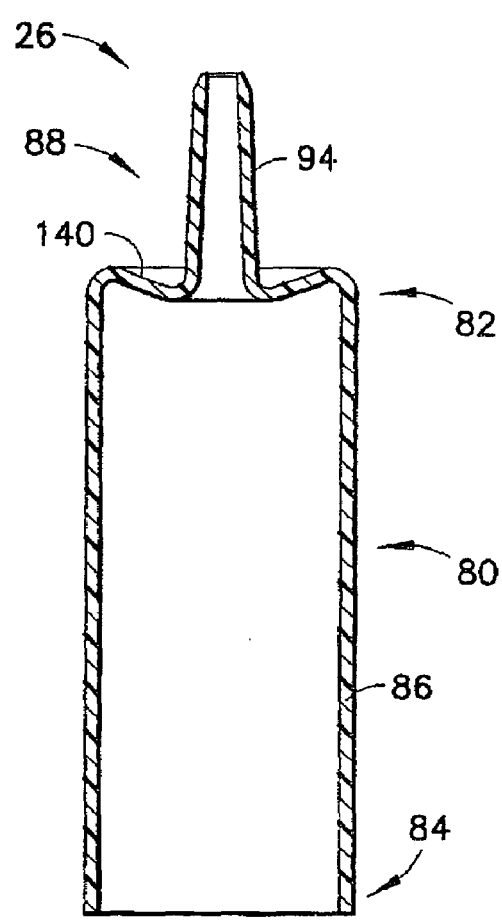
FIG. 17
FIG. 18

PRESSURE JACKET SYSTEM WITH PIVOTAL LOCKING MEMBERS

BACKGROUND OF THE INVENTION

This invention relates generally to pressure jacket systems for securing a syringe to an injector, to syringes for use with pressure jacket systems, and to methods of loading syringes in and removing syringes from pressure jacket systems. More specifically, the invention relates to front-loading pressure jacket systems and methods for allowing front-loading and removal of syringes therefrom, and to syringes of special construction for use with, for example, pressure jackets.

In the medical field, patients are often injected with fluids in procedures such as angiography, computed tomography (CT), and magnetic resonance imaging (MRI). In such procedures, which require controlled injection of relatively large volumes of fluid into a patient, a catheter is used as a conduit for the fluid, which is connected to the syringe(s) by a connector tube. The syringe(s) is mounted on a motorized injector having an injector head.

For compatibility with injectable fluids, syringes may be made of glass or polymeric materials, such as polypropylene, with a certain minimum wall thickness. The thickness is critical as typical pressures of up to 1200 p.s.i. (i.e., in angiographic procedures) are used to inject the fluids into a patient.

Pressure jackets are known in the art in at least two varieties, breech or rear loading and front-loading, for substantially enclosing and retaining syringes while in use. A pressure jacket serves to limit radial expansion of a syringe, which may lead to bursting or to leaks of the pressurized fluid around the seal(s) of the syringe plunger. Another function of a pressure jacket is to prevent forward motion of the syringe. For example, typically a force of 2000 pounds is required to restrain the forward motion of a 200 ml syringe with a cross section of 1.7 $in^2$ at 1200 p.s.i.

U.S. Pat. No. 4,677,980, the contents of which are incorporated herein by reference, discloses an angiographic injector apparatus in which syringes are rear loaded into a pressure jacket of the injector. More specifically, the apparatus comprises a rotatable turret that carries a pair of the pressure jackets and which is rotatable so that when one of the pressure jackets, into which a syringe has been rear loaded, is in an injection position the other pressure jacket is in a position in which an associated syringe may be rear loaded. Subsequently, when injection of contrast media from the first syringe is completed, the turret is rotated to move the first syringe to an unloading-loading position, with the second pressure jacket and the second syringe concurrently being moved into the injection position.

A disadvantage of rear loading pressure jacketed injectors is that, after an injection, the patient tubing typically must be disconnected from the syringe before the syringe may be extracted from the rear of the pressure jacket and discarded. Not only does this operation expend valuable operator time but fluids, such as contrast fluid and blood, may drip or spill from the syringe or the tubing after the tubing is removed from the syringe, thereby creating a potentially unsafe or hazardous condition. Additionally, fluid spilled during loading and purging of air from the syringe may migrate inside the pressure jacket and the injector and require cleaning.

Motivated at least in part by this concern, front-loading injectors (pressure jacketed and non-pressure jacketed injectors) have been developed. U.S. Pat. Nos. 5,300,031; 5,779,675; and 5,800,397, for example, disclose front-loading pressure jacketed injector systems and U.S. Pat. No. 5,383,858 discloses front-loading pressure jacketed and non-pressure jacketed injector systems. The contents of U.S. Pat. Nos. 5,300,031, 5,779,675, 5,800,397 and 5,383,858 are incorporated herein by reference.

U.S. Pat. No. 5,300,031 discloses various embodiments of a pressure jacketed injector system wherein a syringe is loaded into and removed from an injector pressure jacket through an opening provided in the front end of the pressure jacket. To retain the syringe within the pressure jacket, for example during an injection operation, the front end of the syringe is locked to the front end of the pressure jacket.

U.S. Pat. No. 5,779,675 also discloses various embodiments of front-loading pressure jacketed injector systems. In a number of embodiments, for example as shown in FIGS. 12-16 of the '675 patent, one or more retaining plates or walls preferably supported by one or more arms or rods retain a syringe within the pressure jacket. The retaining plates or walls are preferably moved between open and closed positions to allow syringes to be inserted into and removed from the pressure jackets.

While front-loading pressure jacketed injector systems are known in the art, improvements in the design of such pressure jacketed injector systems and also in the design of syringes used in both pressure jacketed and non-pressure jacketed injector systems are and continue to be highly desirable.

SUMMARY OF THE INVENTION

The present invention relates generally to a fluid injection apparatus for use with a syringe. The fluid injection apparatus comprises a housing defining a central opening and a drive piston extendable through the central opening for imparting motive forces to a syringe plunger disposed within the syringe. The fluid injection apparatus further comprises a pressure jacket assembly associated with the housing for securing the syringe during an injection procedure. The pressure jacket assembly preferably comprises a pressure jacket associated with the housing and aligned with the central opening, and at least one locking member pivotally associated with the pressure jacket for cooperating with the syringe. The at least one locking member is configured to engage a distal end of the syringe. The at least one locking member is movable between an engaged position cooperating with the syringe and preventing removal thereof from the pressure jacket and a disengaged position for allowing insertion and removal of the syringe. A distal end of the pressure jacket may define a syringe receiving opening for receiving the syringe and a proximal end of the pressure jacket may be removably associated with the housing. The pressure jacket may be made of substantially clear plastic.

The fluid injection apparatus may further comprise an actuation ring rotationally associated with the distal end of the pressure jacket and be configured to move the at least one locking member between the engaged and disengaged positions. The distal end of the pressure jacket may comprise a radially outward extending flange and the actuation ring may be rotationally associated with the flange for moving the at least one locking member between the engaged and disengaged positions.

The at least one locking member preferably defines at least one groove configured to engage at least one ridge formed on the syringe. In the engaged position, the at least one ridge engages with the at least one groove.

The at least one locking member may comprise a first end pivotally associated with the flange and a second end having a syringe engaging surface defining the at least one groove. The syringe engaging surface may define a curved shape for cooperating with a cylindrically shaped syringe, which may comprise an injection section having a conical portion and an elongated injection neck. With the at least one locking member in the engaged position, the curved syringe engaging surface may cooperate with the conical portion to secure the syringe during the injection procedure.

The at least one locking member may comprise a first end pivotally associated with the distal end of the pressure jacket. The actuation ring may comprise at least one tab member formed on an inner surface thereof and configured to coact with the first end for moving the at least one locking member between the engaged and disengaged positions.

The first end may comprise a radially outward extending projection and the at least one tab member may comprise a pair of tab members positioned on opposite sides of the projection such that rotational movement of the actuation ring causes the tab members to coact with the projection and move the at least one locking member between the engaged and disengaged positions.

A distal end wall of the actuation ring may taper inward toward a central axis of the pressure jacket for guiding the syringe during insertion thereof into the pressure jacket.

The at least one locking member may comprise a plurality of locking members. The actuation ring may be configured to move the locking members between the engaged and disengaged positions. The locking members may be regularly spaced around the distal end of the pressure jacket. The distal end of the pressure jacket may comprise a radially outward extending flange and the actuation ring may be rotationally associated with the flange for moving the locking members between the engaged and disengaged positions. The locking members preferably each define at least one groove configured to engage at least one ridge formed on the syringe. In the engaged position, the ridge(s) formed on the syringe engages with the groove(s) in the locking members. The locking members may each comprise a first end pivotally associated with the flange and a second end having a syringe engaging surface preferably defining the at least one groove for engaging the at least one ridge preferably formed on the syringe. The syringe engaging surface of each of the locking members may define a curved shape for engaging the cylindrically shaped syringe. The curved syringe engaging surfaces of the locking members may cooperate with the conical portion of the cylindrical syringe to secure the syringe during the injection procedure.

The locking members may each comprise a first end pivotally associated with the distal end of the pressure jacket. The actuation ring may comprise a plurality of tab members formed on an inner surface thereof and configured to coact with the first ends of the locking members, respectively, for moving the locking members between the engaged and disengaged positions. The first end of each of the locking members may comprise a radially outward extending projection. The tab members may be arranged in pairs. The pairs of tab members may be positioned on opposite sides of the projections, respectively, such that rotational movement of the actuation ring causes the tab members to coact with the projections and move the locking members between the engaged and disengaged positions.

The at least one locking member may be pivotal in a plane substantially normal to the longitudinal axis of the pressure jacket.

Another embodiment of the fluid injection apparatus of the present invention comprises a syringe and an injector. The syringe has a cylindrical body comprising an injection section having a conical portion. The conical portion defines at least one ridge. A plunger is movably received in the body. The injector comprises a housing defining a central opening and a drive piston extendable through the central opening for imparting motive forces to the plunger disposed within the body. The injector further comprises a pressure jacket assembly associated with the housing for securing the syringe during an injection procedure. The pressure jacket assembly comprises a pressure jacket associated with the housing and aligned with the central opening. The pressure jacket assembly further comprises at least one locking member pivotally associated with the pressure jacket for cooperating with the syringe. The at least one locking member defines at least one groove configured to engage the at least one ridge formed on the conical portion. The at least one locking member is movable between an engaged position cooperating with the conical portion and preventing removal of the syringe from the pressure jacket and a disengaged position for allowing insertion and removal of the syringe. In the engaged position, the at least one ridge engages with the at least one groove.

The present invention also relates generally to a pressure jacket used in a fluid injection procedure. The pressure jacket is adapted to receive a syringe used in the fluid injection procedure. The pressure jacket comprises an elongated body having a proximal end configured to be removably associated with a fluid injection apparatus. The pressure jacket further comprises at least one locking member pivotally associated with the body for engaging the syringe. The at least one locking member is movable between an engaged position cooperating with the syringe and preventing removal thereof from the body and a disengaged position for allowing insertion and removal of the syringe.

A further embodiment of the fluid injection apparatus of the present invention comprises a housing and a pressure jacket assembly. The housing defines a central opening and includes a drive piston extendable through the central opening for imparting motive forces to a syringe plunger disposed within the syringe. The pressure jacket assembly is associated with the housing for securing the syringe during an injection procedure. The pressure jacket assembly comprises a pressure jacket associated with the housing and aligned with the central opening. The pressure jacket defines a syringe receiving opening for receiving the syringe. The pressure jacket assembly further comprises at least one of locking member pivotally associated with the pressure jacket. The at least one locking member is movable between a disengaged position allowing the syringe to be inserted into the pressure jacket and removed therefrom through the syringe receiving opening and an engaged position wherein the at least one locking member defines a reduced diameter opening in the syringe receiving opening preventing insertion into and removal of the syringe through the syringe receiving opening.

Another embodiment of the pressure jacket of the present invention comprises an elongated body having a proximal end configured to be removably associated with a fluid injection apparatus and a distal end defining a syringe receiving opening for receiving a syringe. The pressure jacket further comprises at least one locking member pivotally associated with the body. The at least one locking member is movable between a disengaged position allowing the syringe to be inserted into the body and removed therefrom through the syringe receiving opening and an engaged position wherein the at least one locking member defines a reduced diameter opening in the syringe receiving opening preventing insertion into and removal of the syringe through the syringe receiving opening.

Further, the present invention relates generally to syringes, preferably disposable syringes, for use with pressure jacket systems generally. The syringe is used to inject a liquid medium into the body of the patient. The syringe comprises a body comprising a cylindrical main body, a conical portion connected to the main body, and a discharge outlet connected to the conical portion. The conical portion defines at least one ridge disposed or formed on the conical portion. In a preferred embodiment, the at least one ridge extends circumferentially around the conical portion. In an alternate embodiment, the at least one ridge may be segmented (non-continuous) or formed as a number of ridges extending along or around the conical portion. The at least one ridge may comprise three ridges extending circumferentially around the conical portion.

Another embodiment of the syringe of the present invention comprises a body comprising a cylindrical main body and a discharge outlet formed at one end of the main body. The one end of the main body defines a concave shoulder extending around the discharge outlet.

Furthermore, the present invention relates generally to methods of loading a syringe to an injector. The syringe comprises a body comprising a cylindrical main body, a conical portion at a distal end of the syringe and connected to the main body, and a discharge outlet connected to the conical portion. A plunger is movably disposed within at least a portion of the main body. The injector comprises a pressure jacket assembly comprising a pressure jacket associated with the injector. The pressure jacket comprises at least one locking member pivotally associated with the pressure jacket for engaging the syringe and an actuation ring rotationally associated with the pressure jacket for moving the at least one locking member between an engaged position cooperating with the conical portion and preventing removal of the syringe from the pressure jacket and a disengaged position allowing insertion and removal of the syringe. The method may comprise the steps of inserting a proximal end of the syringe into the pressure jacket, and rotating the actuation ring to move the at least one locking member to the engaged position cooperating with the conical portion of the syringe. The method may further comprise the steps of rotating the actuation ring in the opposite direction to move the at least one locking member to the disengaged position, and removing the syringe from the pressure jacket. Additionally, the method may comprise the steps of connecting the plunger to a drive piston of the injector, and advancing the drive piston to move the plunger within the main body of the syringe.

Further, the at least one locking member may define at least one groove and the conical portion of the syringe may define at least one ridge, such that in the engaged position the at least one ridge engages with the at least one groove. When the actuation ring is rotated in the opposite direction to move the at least one locking member to the disengaged position, the at least one ridge may disengage from the at least one groove.

Another embodiment of the method also involves loading a syringe to an injector. The syringe comprises a body comprising a cylindrical main body and a discharge outlet formed at one end of the main body. The one end of the main body defines a concave shoulder extending around the discharge outlet. A plunger is movably disposed within at least a portion of the main body. The injector comprises a pressure jacket assembly comprising a pressure jacket associated with the injector. The pressure jacket defines a syringe receiving opening for receiving the syringe. The pressure jacket comprises at least one locking member pivotally associated with the pressure jacket. The pressure jacket assembly further comprises an actuation ring rotationally associated with the pressure jacket for moving the at least one locking member between a disengaged position allowing the syringe to be inserted into the pressure jacket and removed therefrom through the syringe receiving opening and an engaged position wherein the at least one locking member defines a reduced diameter opening in the syringe receiving opening having a smaller diameter than the concave shoulder. Generally, the method comprises the steps of inserting the syringe into the syringe receiving opening in the pressure jacket with the discharge outlet substantially extending outward from the pressure jacket, and rotating the actuation ring to move the at least one locking member to the engaged position defining the reduced diameter opening, preventing passage of the concave shoulder through the syringe receiving opening and removal of the syringe from the pressure jacket.

Further details and advantages of the present invention will become apparent from the following detailed description when read in conjunction with the drawings wherein like parts are designated with like reference characters throughout.

BRIEF DESCRIPTION OF THE DRAWINGS

FIG. 17 is a side view of the syringe of FIG. 16;

FIG. 18 is a cross sectional view taken along line 18-18 in FIG. 17;

DETAILED DESCRIPTION OF PREFERRED EMBODIMENTS

Figure 1:
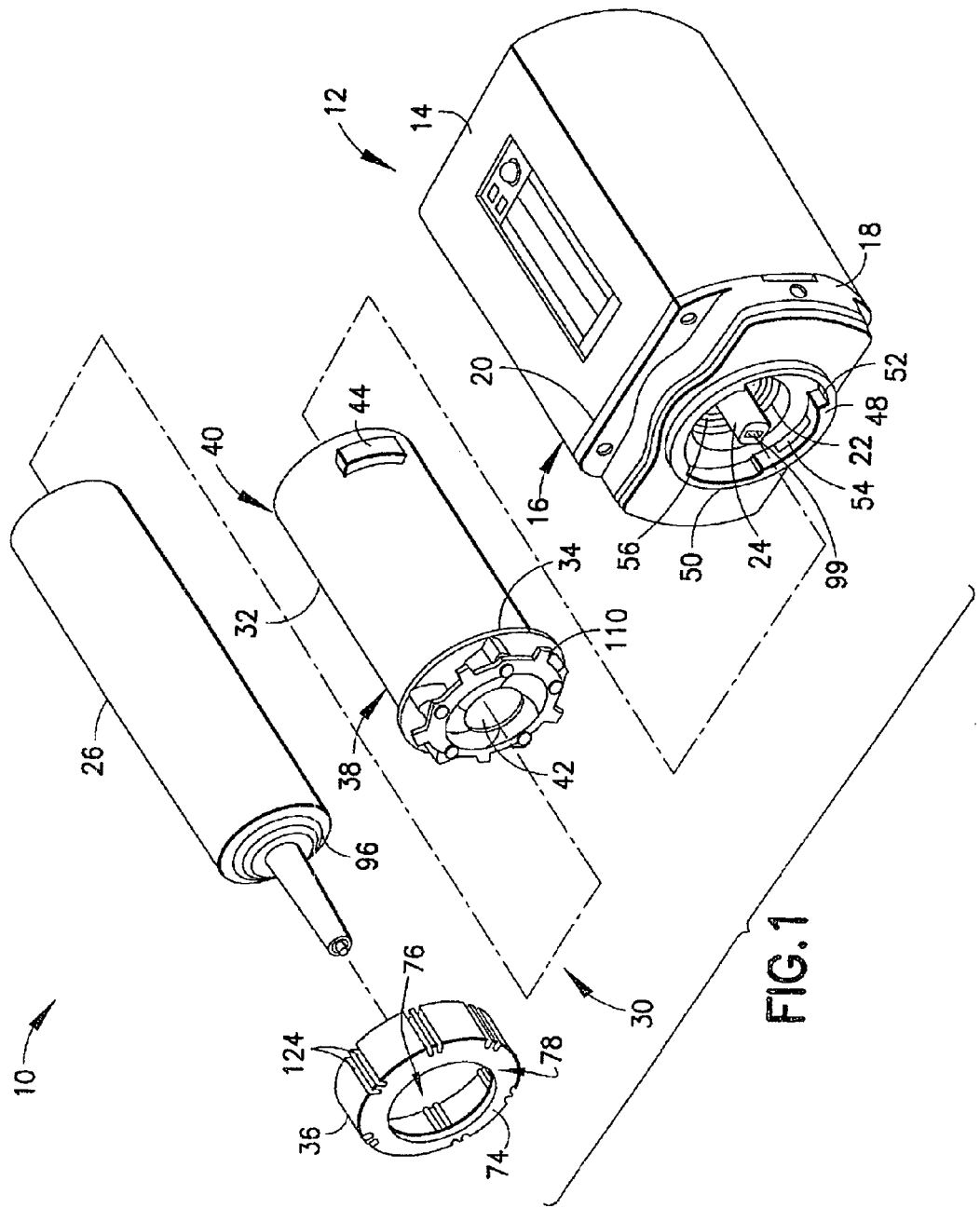
FIG. 1 is an exploded perspective view of a fluid injection apparatus in accordance with the present invention and comprising an injector, pressure jacket assembly, and syringe.

FIG. 1 shows a fluid injection apparatus 10 in accordance with a first embodiment of the present invention. The fluid injection apparatus 10 comprises an injector head 12, which may be supported on a support structure (not shown). The injector head 12 comprises an injector housing 14 having a front end 16. A faceplate 18 is attached to and encloses the front end 16 of the housing 14. The faceplate 18 may be secured to the front end 16 of the housing 14 by conventional means (i.e., mechanical fasteners and the like) or integrally formed with the housing 14.

The housing 14 defines a central opening 20 aligned with a central passage 22 defined in the faceplate 18. The injector head 12 further comprises an injector drive piston 24, which is extendable through the central opening 20 and central passage 22. The details of the injector head 12 and, more particularly, the injector drive piston 24 are described in U.S. Pat. No. 5,383,858, which was previously incorporated herein by reference. The injector head 12 is intended to carry and support a syringe 26 used in a fluid injection procedure as discussed further hereinafter.

A pressure jacket assembly 30 is associated with the injector head 12. The pressure jacket assembly 30 carries and supports the syringe 26 used in the fluid injection procedure, such as an angiographic procedure. The pressure jacket assembly 30 is configured to project outward from the front end 16 of the housing 14 and support the syringe 26 during the fluid injection procedure. The pressure jacket assembly 30 is generally comprised of a front-loading pressure jacket 32 having at least one locking member 34 associated therewith and an actuation ring 36. The actuation ring 36 is shown detached from the pressure jacket 32 in FIG. 1, but in the preferred embodiment of the fluid injection apparatus 10 the actuation ring 36 is rotationally associated with the pressure jacket 32. The faceplate 18 may also be considered part of the pressure jacket assembly 30 in an alternative embodiment of the fluid injection apparatus 10.

The pressure jacket 32 is a generally cylindrical structure having a front or distal end 38 and a rear or proximal end 40. As used in this disclosure, the term "proximal" refers to the injector facing side of a given element and the term "distal" refers to the syringe facing side of a given element. The distal end 38 of the pressure jacket defines a syringe receiving mouth or opening 42 for receiving the syringe 26 into the pressure jacket 32. The proximal end 40 of the pressure jacket 32 is configured to removably engage with the faceplate 18. The presently preferred removable connection between the pressure jacket 32 and the faceplate 18 is a bayonet socket connection. For this purpose, the proximal end 40 of the pressure jacket 32 comprises a pair of oppositely facing bayonet projections 44, 46. The bayonet projections 44, 46 are formed to cooperate with a flange 48 extending outward from the faceplate 18. The flange 48 defines a pair of opposing recesses 50, 52 formed to receive the bayonet projections 44, 46. The flange 48 further defines a pair of opposing bayonet receiving slots 54, 56. The bayonet projections 44, 46 may be inserted into the flange 48 through the recesses 50, 52 and then rotated to engage the bayonet receiving slots 54, 56 to secure the pressure jacket 32 to the faceplate 18. The bayonet receiving slots 54, 56 may be formed so that, for example, a one-quarter (¼) turn of the pressure jacket 32 after being inserted into the recesses 50, 52 will fully insert the bayonet projections 44, 46 into the bayonet receiving slots 54, 56 and secure the pressure jacket 32 to the faceplate 18. The above-described bayonet socket connection may be replaced by any substantially equivalent mechanical connection, such as a threaded connection and the like.

The pressure jacket 32 is typically made of a material capable of restraining the outward expansion of the syringe 26 during a fluid injection procedure. As discussed previously, the syringe 26 by itself is typically not capable of withstanding the high pressures associated with certain injection procedures, such as angiography. The pressure jacket 32, as is well known in the art, is used to limit the radial expansion of the syringe 26, which may lead to bursting or leaking, as discussed previously. Typically, the syringe 26 is made of relatively inexpensive medical grade plastic material and is intended to be disposable (i.e., single use). Typical plastics for the syringe 26 include polypropylene, polyethylene, and polycarbonate. The pressure jacket 32 is reusable and made of a material capable of withstanding pressures up to 1200 psi and higher. For example, the pressure jacket 32 may be made of metal such as steel or aluminum. However, it is advantageous for the syringe 26 to be visible through the pressure jacket 32 so that an operator of the fluid injection apparatus 10 may view the syringe 26 during the fluid injection procedure. Accordingly, the pressure jacket 32 is preferably made of a substantially clear plastic material, such as polycarbonate, for viewing the syringe 26 during a fluid injection procedure. The pressure jacket 32 preferably has an inner diameter sized to smoothly, but snugly receive the outer diameter of the syringe 26. A typical clearance between the outer diameter of the syringe 26 and the inner diameter of the pressure jacket 32 may be about 0.005 inches. Further details of the pressure jacket assembly 30 and syringe 26 will be discussed hereinafter.

Figure 2:
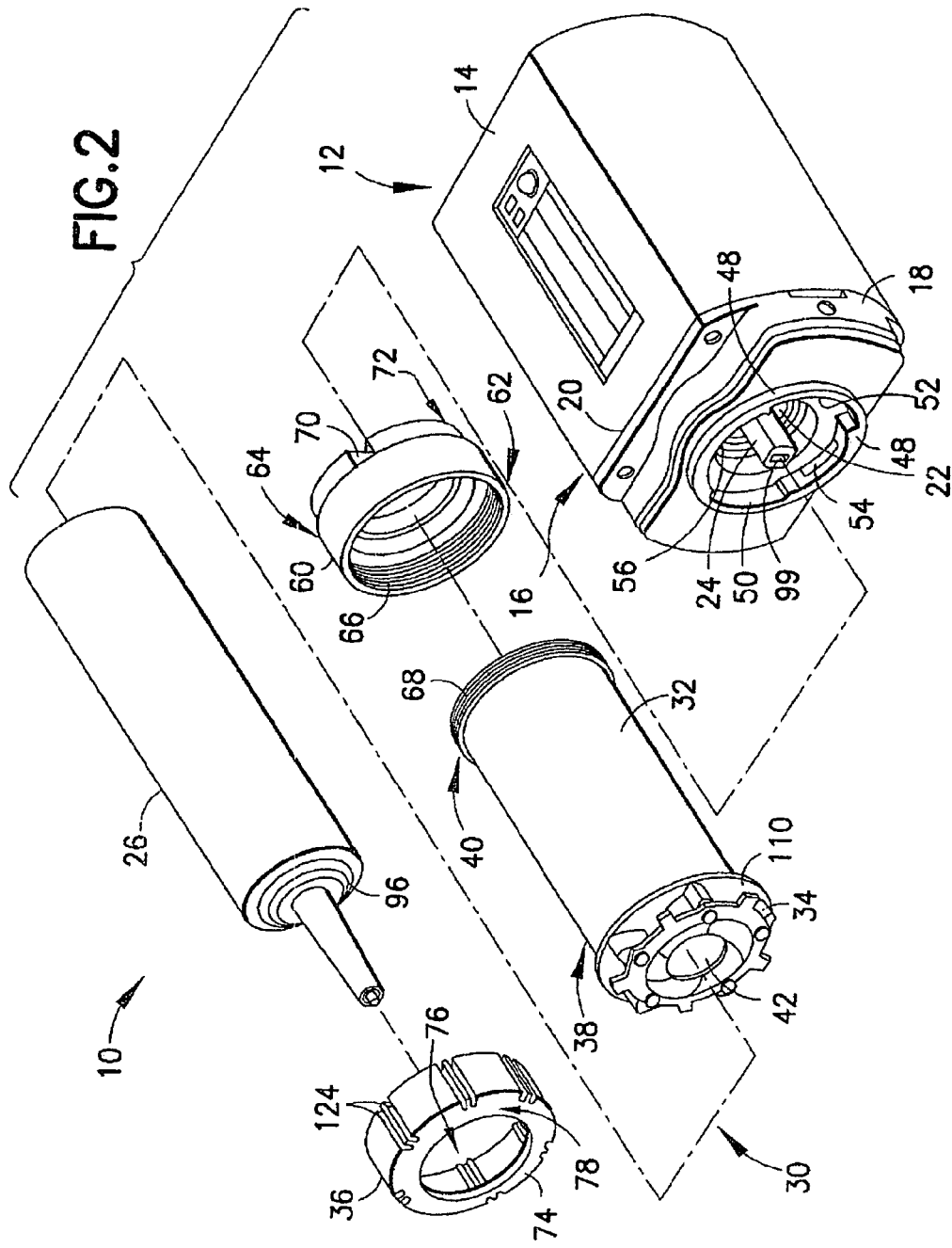
FIG. 2 is an exploded perspective view of the fluid injection apparatus of FIG. 1 showing an alternative embodiment of the pressure jacket assembly.

Referring to FIG. 2 an alternative embodiment of the fluid injection apparatus 10 is shown and comprises a slightly modified pressure jacket assembly 30. The pressure jacket assembly 30 of FIG. 2 is substantially similar to the pressure jacket assembly 30 of FIG. 1, with the addition of a cylindrically shaped coupling member 60. The coupling member 60 is cylindrically shaped in a similar manner to the pressure jacket 32. The coupling member 60 has a front or distal end 62 configured for removable connection to the pressure jacket 32 and a rear or proximal end 64 configured for removable connection to the faceplate 18. The distal end 62 of the coupling member 60 preferably defines internal threads 66. The internally threaded distal end 62 of the coupling member 60 is adapted to receive the proximal end 40 of the pressure jacket 32. The proximal end 40 of the pressure jacket 32, in this embodiment, preferably defines external threads 68 configured to cooperate with the internally threaded distal end 62 of the coupling member 60 to removably secure the pressure jacket 32 to the coupling member 60. A threaded connection between the pressure jacket 32 and the coupling member 60 is presently preferred, but equivalent mechanical connections may be used in place of the threaded connection. The threaded connection between the pressure jacket 32 and coupling member 60 may be conventional (i.e., clockwise rotation for engagement, counterclockwise rotation for disengagement). However, the conventional arrangement may be reversed in accordance with the present invention. The coupling member 60 may be made of any of the materials discussed previously in connection with the pressure jacket 32, with aluminum being the presently preferred material for the coupling member 60, but polycarbonate is also a suitable material for the coupling member 60.

A bayonet socket connection similar to that shown in FIG. 1 may be used to removably connect the coupling member 60 to the faceplate 18. For this purpose, the proximal end 64 of the coupling member 60 comprises a pair of oppositely facing bayonet projections 70, 72. The bayonet projections 70, 72 are positioned to cooperate with the flange 48 extending outward from the faceplate 18. The bayonet projections 70, 72 may be inserted into the flange 48 through the recesses 50, 52 defined in the flange 48 and then rotated to engage the bayonet receiving slots 54, 56 to secure the coupling member 60 to the faceplate 18. The bayonet connection between the coupling member 60 and the faceplate 18 is preferably configured so that the engagement of the bayonet projections 70, 72 in the bayonet receiving slots 54, 56 facilitates threading of the proximal end 40 of the pressure jacket 32 into the distal end 62 of the coupling member 60 securing their engagement. The bayonet socket connection between the coupling member 60 and the faceplate 18 may be replaced by any equivalent mechanical connection.

Referring to FIGS. 1 and 2, the actuation ring 36 is annular shaped and has a distal end wall 74 with an inner side or surface 76 and an outer side or surface 78. The inner side 76 faces the distal end 38 of the pressure jacket 32. The outer side 78 forms the end surface of the pressure jacket 32. Preferably, the distal end wall 74 (i.e., outer side 78) tapers inward toward a central longitudinal axis L of the pressure jacket 32. The tapered form of the distal end wall 74 facilitates the front-loading of the syringe 26 into the pressure jacket 32. In particular, the tapered distal end wall 74 (i.e., outer side 78) guides the syringe 26 into the syringe receiving opening 42 in the pressure jacket 32 during a syringe loading operation.

Figure 3:
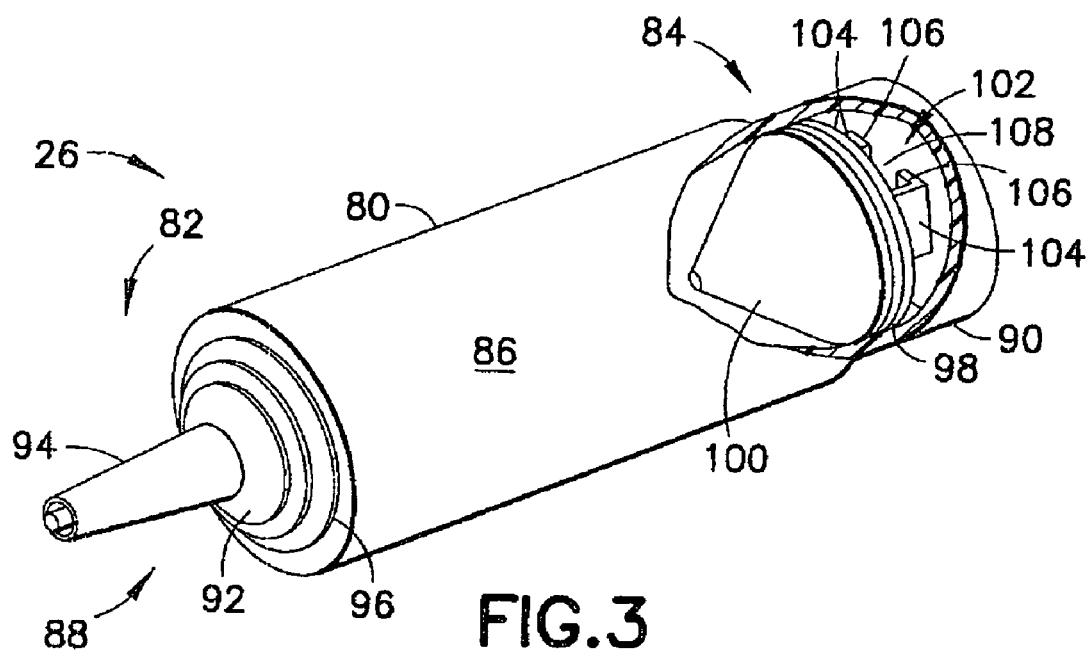
FIG. 3 is a perspective and partially cutaway view of the syringe used in the fluid injection apparatus of FIG. 1.

Referring to FIG. 3, the syringe 26 used with the fluid injection apparatus 10 generally comprises an elongated syringe body 80 having a front or distal end 82 and a rear or proximal end 84. The syringe body 80 comprises a generally cylindrical center section or main body 86, an injection section 88 formed at the distal end 82 of the syringe body 80, and, preferably, an expansion section 90 formed at the proximal end 84 of the syringe body 80. The generally cylindrical center section or main body 86 has a relatively uniform outer diameter sized to be received into the syringe receiving opening 42 in the pressure jacket 32. The injection section 88 comprises a generally conical portion 92 and an elongated injection neck 94, which has a relatively small inner diameter compared to the inner diameter of the center section 86. The conical portion 92 generally tapers from the center section 86 to the elongated injection neck 94. The conical portion 92 is formed with at least one and, preferably, a plurality of raised ridges 96. The function of the ridges 96 will be discussed further hereinafter. The ridges 96 may extend circumferentially around the conical portion 92 or be segmented (i.e., non-continuous) on the conical portion 92.

A syringe plunger 98 is preferably preloaded into the syringe 26. The syringe plunger 26 is configured for connection to the drive piston 24 of the injector 12. The drive piston 24 is extendable through the central opening 20 in the housing 14 and the central passage 22 in the faceplate 18 for imparting motive forces to the syringe plunger 98 disposed within the syringe 26. The injector drive piston 24 includes a rectangular injector end plate 99, which is adapted to engage the syringe plunger 98 and impart motion to the syringe plunger 98. The end plate 99 may be lighted to provide light to the syringe 26 during an injection procedure. The syringe plunger 98 is generally conical shaped to cooperate with the conical portion 92 of the injection section 88. The syringe plunger 98 includes a tapered, conical-shaped front end 100 and a coupling end 102 that faces the proximal end 84 of the syringe body 80. In the preferred embodiment, a pair of flexible lugs or coupling members 104 extend outward from the coupling end 102 for engaging the drive piston 24 and, more particularly, the injector end plate 99 attached to the drive piston 24. The coupling members 104 are flexible and may be integrally formed with the body of the syringe plunger 98, as disclosed in U.S. Pat. Nos. 5,873,861 and 5,947,935, the disclosures of which are incorporated herein by reference. In an alternative embodiment, the coupling members 104 may be substantially fixed or rigid, as described U.S. Pat. No. 4,677,980, which was previously incorporated by reference into this disclosure. The coupling members 104 each have an engagement arm 106. The coupling members 104 define a slot 108 therebetween for receiving the injector end plate 99 of the injector drive piston 24.

Figure 4:
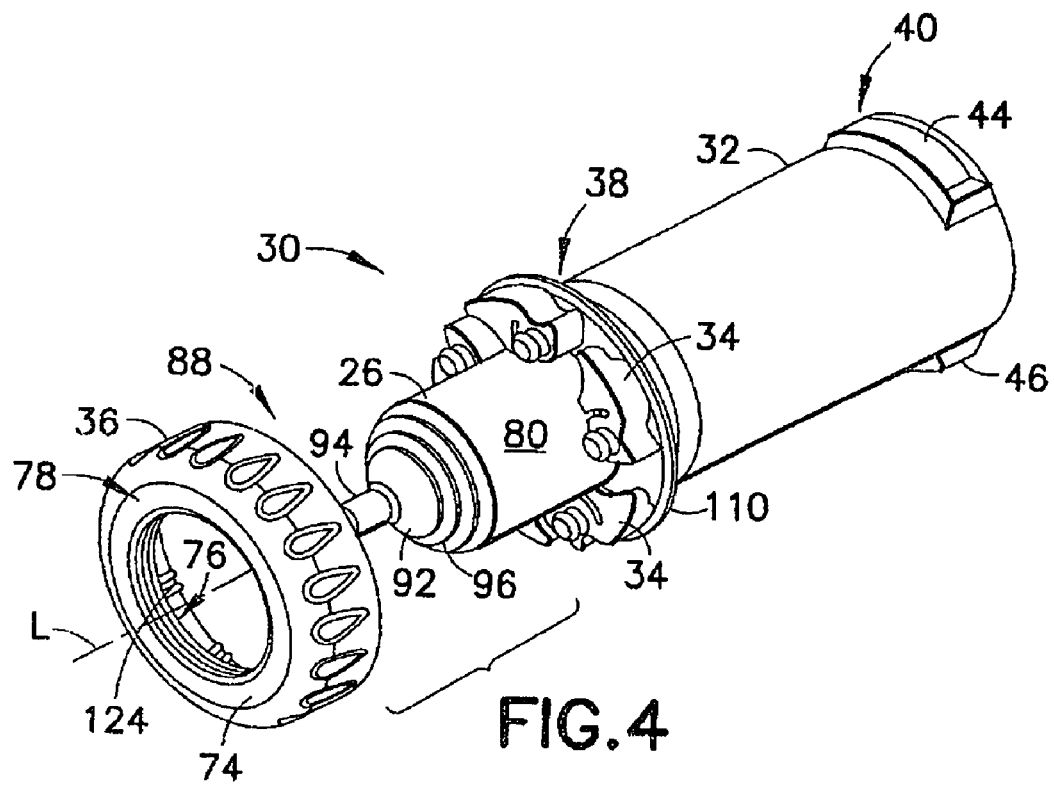
FIG. 4 is a perspective and partially exploded view of the pressure jacket assembly showing the syringe partially loaded into a pressure jacket of the pressure jacket assembly, a plurality of syringe engaging locking members attached to the front end of the pressure jacket, and an actuation ring of the pressure jacket assembly.
Figure 5:
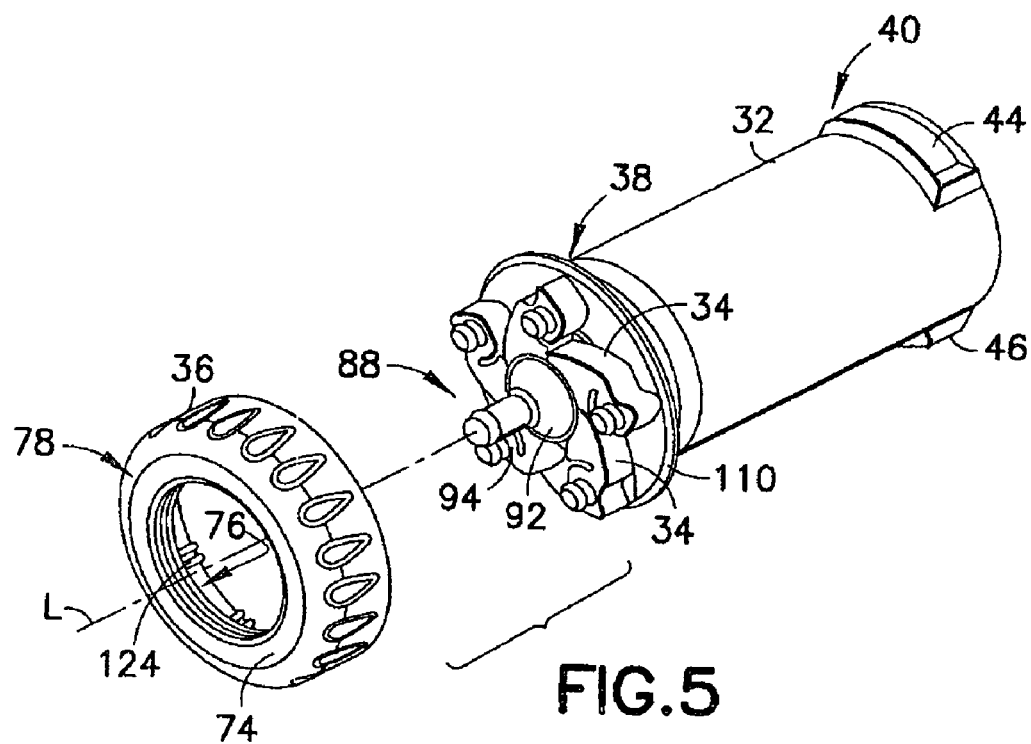
FIG. 5 is a perspective and partially exploded view of the pressure jacket assembly of FIG. 4 showing the syringe fully loaded into the pressure jacket, the plurality of locking members in an engaged position cooperating with the syringe, and the actuation ring.

Referring to FIGS. 1-12, additional details of the pressure jacket assembly 30 will now be described. The pressure jacket assembly 30 further comprises a radially outward extending flange 110 formed at the distal end 38 of the pressure jacket 32. As shown best in FIG. 11, the actuation ring 36 is rotationally associated with the distal end 38 of the pressure jacket 32 and, more particularly, the radially outward extending flange 110. As discussed further herein, the actuation ring 36 is rotationally associated with the flange 110 to move the respective locking members 34 between the engaged and disengaged positions. In FIGS. 4 and 5, the actuation ring 36 is shown detached from the flange 110 to facilitate viewing of the distal end 38 of the pressure jacket 32, locking members 34, and syringe 26.

The locking members 34 are each pivotally associated with the flange 110. The locking members 34 each comprise a first end 112 and a second end 114. The first end 112 of each of the locking members 34 is pivotally connected to the flange 110. The first end 112 of each of the locking members 34 further comprises a projection 116. A recess 118 is defined in the first end 112 of each of the locking members 34 adjacent the pivotal connection point between the first end 112 and the flange 110. The second end 114 of each of the locking members 34 defines a curved syringe engaging surface 120 configured to cooperate with the syringe body 80 during a fluid injection procedure. Preferably, the curved syringe engaging surface 120 is formed to cooperate with the conical portion 92 of the syringe body 80. The curved engaging surface 120 for each of the locking members 34 defines at least one and, preferably, a plurality of grooves 122 configured to receive the ridges 96 formed on the conical portion 92 of the syringe body 80. The locking members 34 may be made of aluminum.

Figure 6:
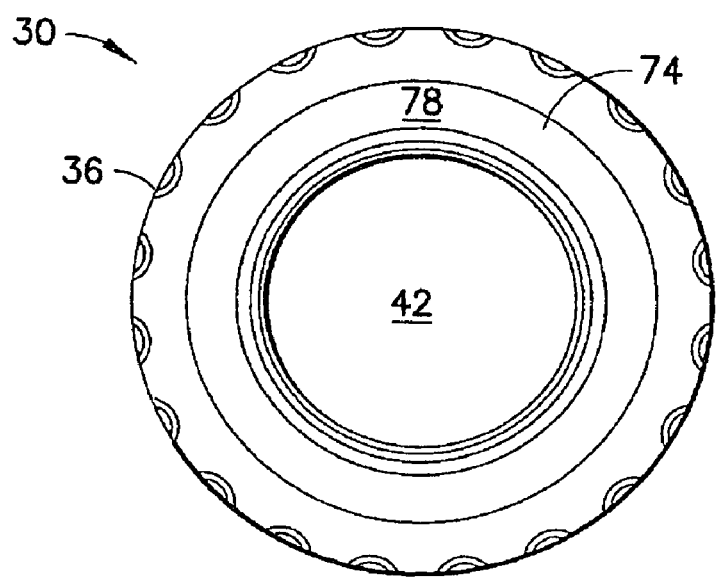
FIG. 6 is an assembled front view of the pressure jacket assembly of FIG. 4 with the syringe omitted for clarity.
Figure 7:
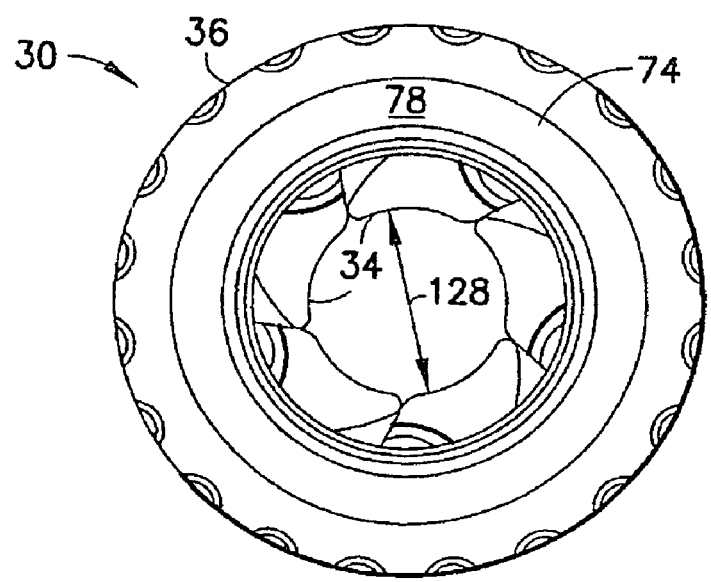
FIG. 7 is an assembled front view of the pressure jacket of FIG. 5 with the syringe omitted for clarity.
Figure 8:
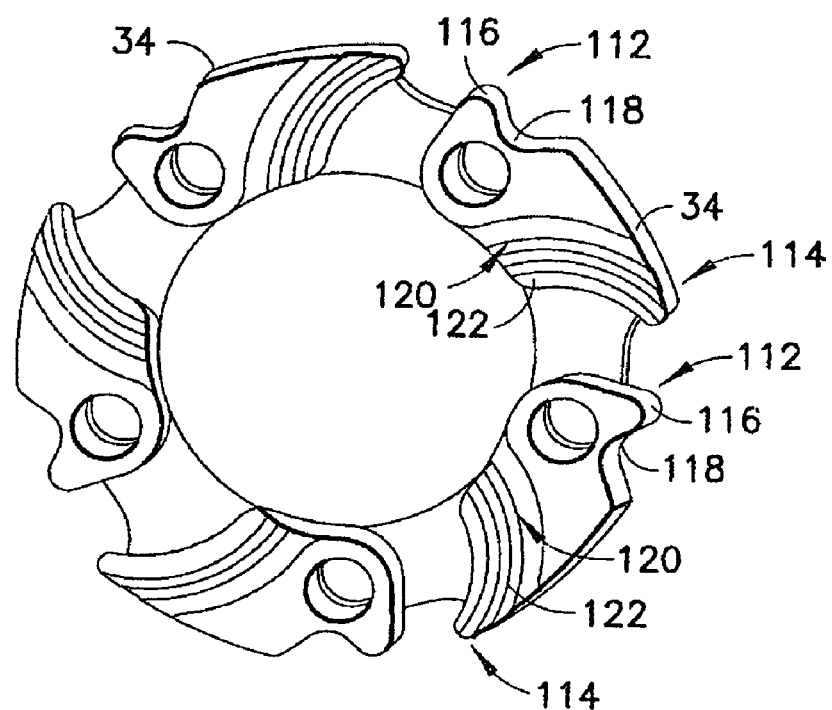
FIG. 8 is a rear view of the plurality of locking members showing the locking members in a syringe disengaged position.
Figure 9:
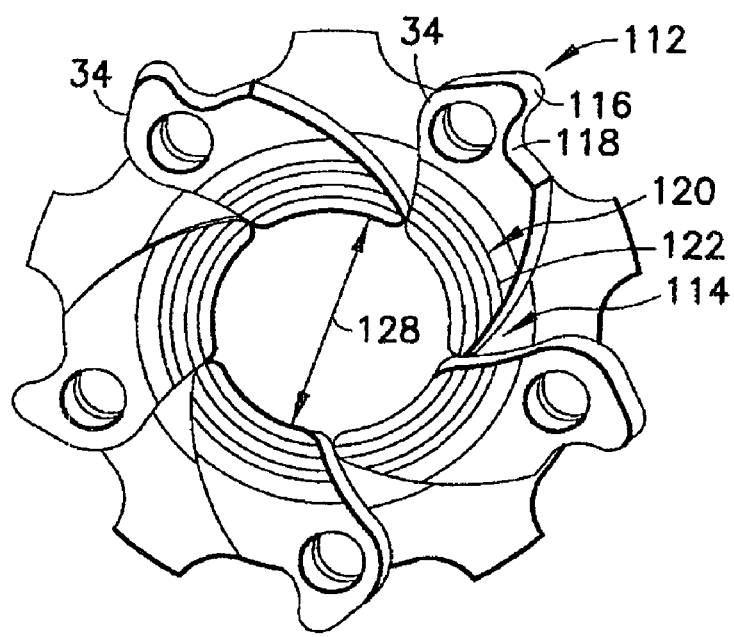
FIG. 9 is a rear view of the plurality of locking members of FIG. 8 showing the locking members in the syringe engaged position.
Figure 10:
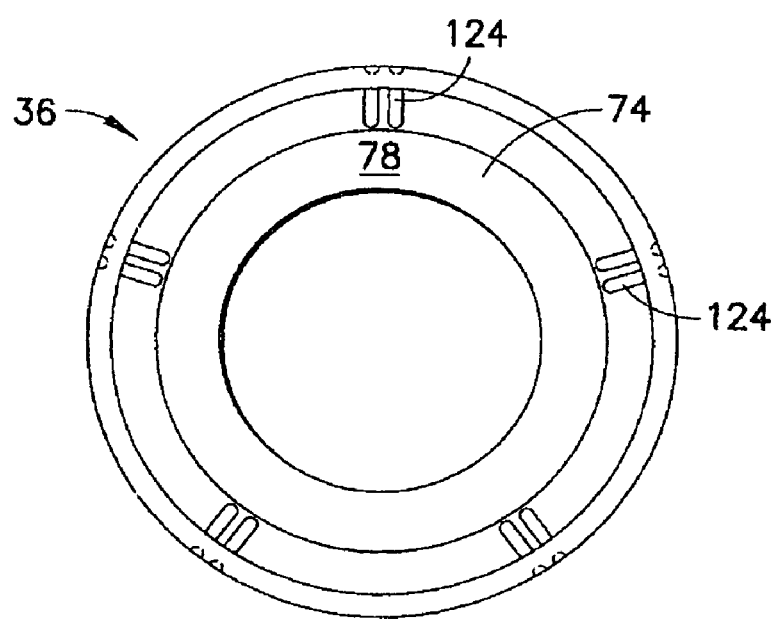
FIG. 10 is a rear view of the actuation ring showing details of the inner side of the distal end wall of the actuation ring.
Figure 11:
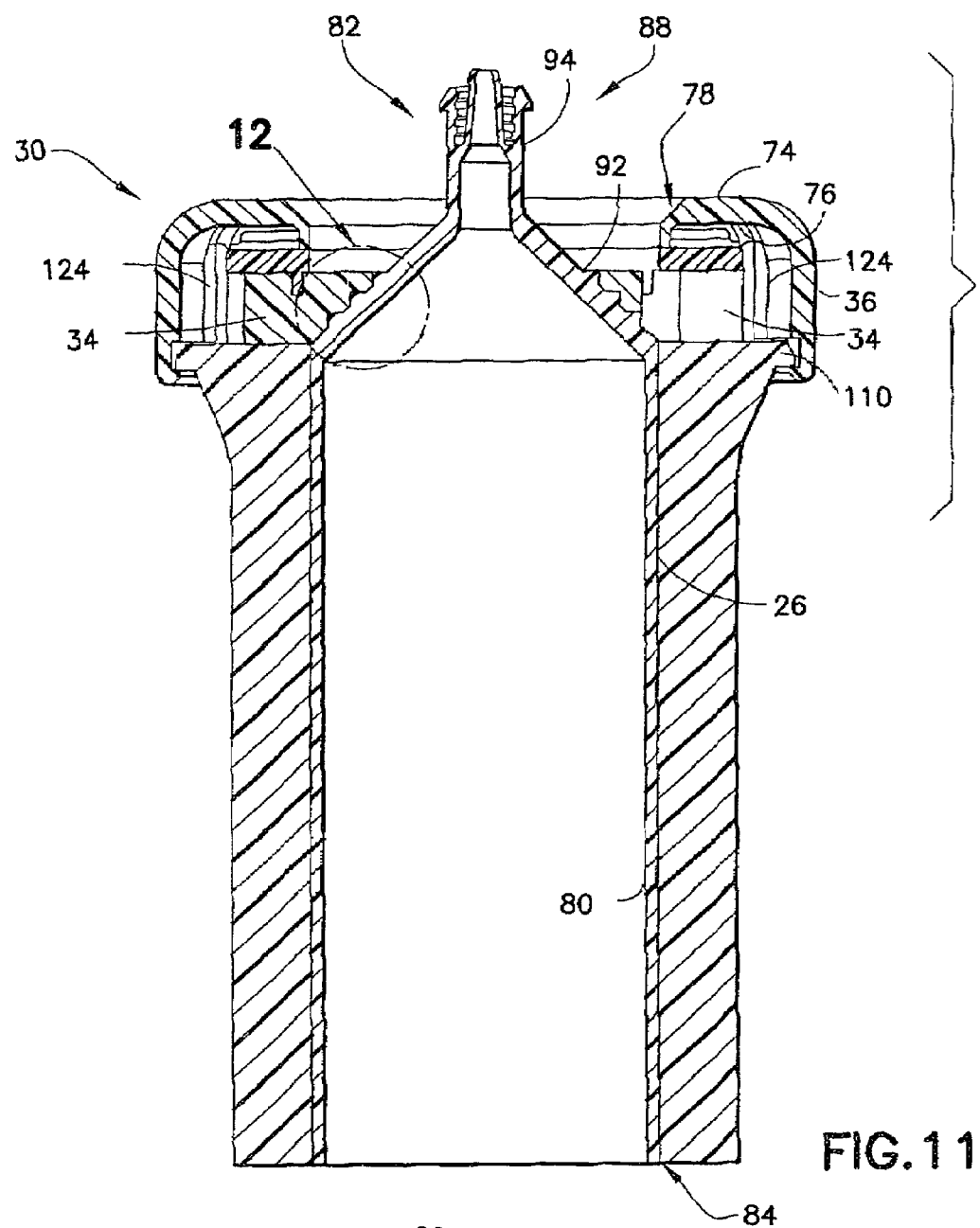
FIG. 11 is a longitudinal cross sectional view of the pressure jacket assembly with the syringe loaded in the pressure jacket and the locking members in the engaged position cooperating with the syringe.
Figure 12:
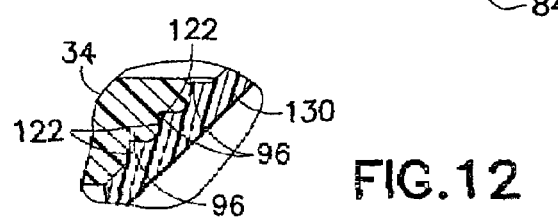
FIG. 12 is a detail view of detail 12 in FIG. 11.

The locking members 34 are generally movable between a disengaged position allowing insertion and removal of the syringe 26 from the pressure jacket 32 and an engaged position wherein the locking members 34 engage or cooperate with the syringe 26 and prevent its removal from the pressure jacket 32. The locking members 34 each preferably move in a plane substantially normal to the longitudinal axis L of the pressure jacket 32. The disengaged position of the locking members 34 is illustrated in FIGS. 4, 6, and 8. The engaged position of the locking members 34 is illustrated in FIGS. 5, 7, and 9. The actuation ring 36 is adapted to move the locking members 34 between the disengaged and engaged positions. For this purpose, the actuation ring 36 comprises a plurality of tab members 124 formed on the inner side or surface 76 of the actuation ring 36, which are configured to coact with the projections 116 formed at the first end 112 of each of the locking members 34 for moving the locking members 34 between the disengaged and engaged positions. The tab members 124 are preferably arranged in pairs, as best shown in FIG. 10. The tab members 124 in each of the pairs of tab members 124 are positioned on opposite sides of the projections 116, respectively. Accordingly, rotational movement of the actuation ring 36 in either direction causes the tab members 124 to coact with the projections 116 to move the locking members 34 between the disengaged and engaged positions. For example, with the locking members 34 in the disengaged position, as shown in FIGS. 4, 6, and 8, rotational movement of the actuation ring 36, for example in a clockwise direction as viewed from the distal end 38 of the pressure jacket 32, causes one of the tab members 124 in each pair of tab members 124 to contact one side of the projections 116 to pivot or rotate the locking members 34 to the engaged position, as illustrated in FIGS. 5, 7, and 9. A subsequent counter clockwise, again as viewed from the distal end 38 of the pressure jacket 32, rotation reverses the operation. In the engaged position, the grooves 122 defined in the curved syringe engaging surfaces 120 of the locking members 34 receive the ridges 96 formed on the conical portion 92 of the syringe body 80.

The locking members 34 are preferably regularly spaced around the radial flange 110 formed at the distal end 38 of the pressure jacket 32. Similarly, the tab members 124 formed on the inner surface 76 of the actuation ring 36 are regularly spaced around the inner surface 76 of the actuation ring 36 to coact with the respective projections 116 on the locking members 34. As best shown in FIGS. 7 and 9, in the engaged position the locking members 34 define a reduced diameter opening 128 that prevents the syringe 26 from moving distally forward and out of the pressure jacket 32 during a fluid injection procedure. During a fluid injection procedure, the locking members 34 are kept in position by means of frictional engagement between the conical portion 92 and the curved syringe engaging surfaces 120 of the locking members 34. In particular, the frictional engagement between the ridges 96 formed on the conical portion 92 of the syringe body 80 and the grooves 122 defined in the syringe engaging surfaces 120 of the locking members 34 maintains the locking members 34 in position during the fluid injection procedure. It will be understood that any number of locking members 34 may be used and the present invention is not limited to the five locking members 34 shown in the various figures.

The procedure for loading, operating, and unloading the fluid injection apparatus 10 with a syringe 26 will now be described with reference to FIGS. 1-12. The pressure jacket 32 is mounted to the injector 12 by inserting the proximal end 40 of the pressure jacket 32 into the flange 48 extending outward from the faceplate 18. In particular, the bayonet projections 44, 46 on the pressure jacket 32 are inserted into the opposing recesses 50, 52 defined by the flange 48. The bayonet projections 44, 46 are then received into the bayonet receiving slots 54, 56 and the pressure jacket 32 is rotated to secure the engagement between the bayonet projections 44, 46 and the bayonet receiving slots 54, 56. An analogous procedure to the foregoing is followed to mount the coupling member 60 and pressure jacket 32 to the faceplate 18 in the alternative embodiment of the pressure jacket assembly 30 shown in FIG. 2, as will be appreciated by those skilled in the art. In general, the coupling member 60 is first mounted to the faceplate 18 and then the pressure jacket 32 is threaded into engagement with the coupling member 60.

With the pressure jacket 32 mounted to the injector 12, the syringe 26 may be inserted into the pressure jacket 32. The locking members 34 are first rotated into the disengaged position as shown, for example, in FIGS. 4, 6, and 8, which allows the rear or proximal end 84 of the syringe body 80 to be received through the actuation ring 36 and into the syringe receiving opening 42 in the pressure jacket 32. The tapered front end wall 74 of the actuation ring 36 guides the insertion of the syringe 26 into the pressure jacket 32.

Once the syringe 26 is fully inserted into the pressure jacket 32, the actuation ring 36 may be rotated to move the locking members 34 from the disengaged to engaged positions. Rotational movement, for example clockwise rotation, of the actuation ring 36 causes the tab members 124 formed on the inner surface 76 of the actuation ring 36 to contact the respective projections 116 formed at the first end 112 of each of the locking members 34. The contact between the tab members 124 and projections 116 causes the locking members 34 to pivot about their respective pivotal connections with the radial flange 110 and move from the disengaged to the engaged positions. In the engaged position, the locking members 34 define the reduced diameter opening 128, which retains the syringe 26 in the pressure jacket 32 during the fluid injection procedure. The locking members 34 are kept in position during the fluid injection procedure by means of frictional engagement between the conical portion 92 of the syringe body 80 and the curved syringe engaging surfaces 120 of the locking members 34. In particular, the frictional engagement between the ridges 96 formed on the conical portion 92 of the syringe body 80 and the grooves 122 defined in the syringe engaging surfaces 120 of the locking members 34 maintains the locking members 34 in position during the fluid injection procedure.

With the locking members 34 in the engaged position cooperating with the conical portion 92 of the syringe body 80, the fluid injection apparatus 10 is now configured for a fluid injection procedure. The syringe 26 may then be placed in fluid communication with a fluid source that is to be injected into the patient. Once the syringe 26 is filled with a desired fluid, the operator may actuate the injector drive piston 24. The drive piston 24 moves forward through the central passage 22 in the faceplate 18 to capture the syringe plunger 98. In particular, the drive piston 24 engages the coupling end 102 of the syringe plunger 98. The drive piston 24 contacts and engages the engagement arms 106 of the coupling members 104 and urges the flexible coupling members 104 apart until the injector end plate 99 of the drive piston 24 is seated in the slot 108 defined between the coupling members 104. The drive piston 24 may then apply motive forces to the syringe plunger 98 to inject the fluid into the patient.

Once the fluid injection procedure is completed, the drive piston 24 is withdrawn into the injector housing 14 and disengaged from the coupling members 104. The syringe 26 may now be replaced with a new syringe 26 for another fluid injection procedure. To remove the used syringe 26, the actuation ring 36 is rotated in the opposite direction, for example counter clockwise direction, to pivot the locking members 34 from the engaged position (FIGS. 5, 7, 9) to the disengaged position (FIGS. 4, 6, 8). The tab members 124 formed on the inner surface 76 of the actuation ring 36 now contact the projections 116 on each of the locking members 34 in the reverse direction to pivot the locking members 34 from the engaged to the disengaged positions. Thereafter, the syringe 26 may be removed from the pressure jacket 32 and replaced by a new syringe 26.

Figure 13:
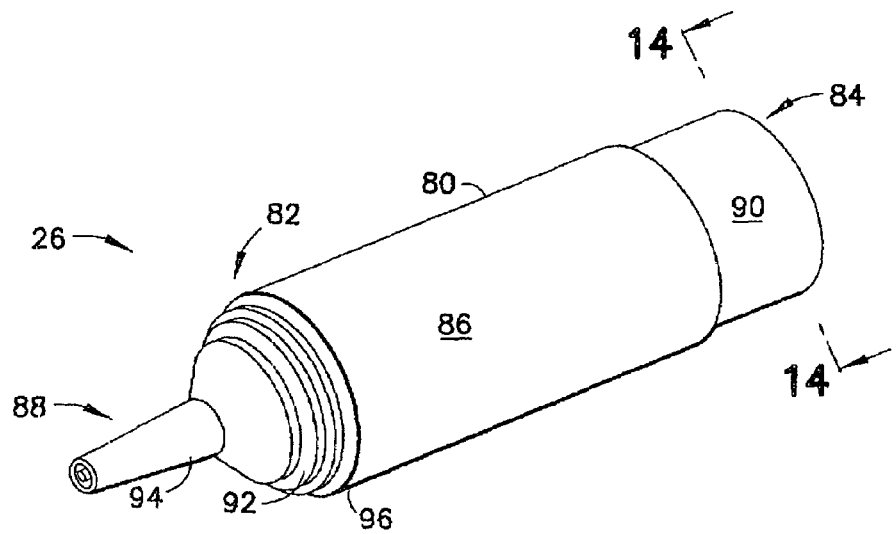
FIG. 13 is a perspective view of one embodiment of the syringe, which may be used in the fluid injection apparatus of the present invention.
Figure 14:
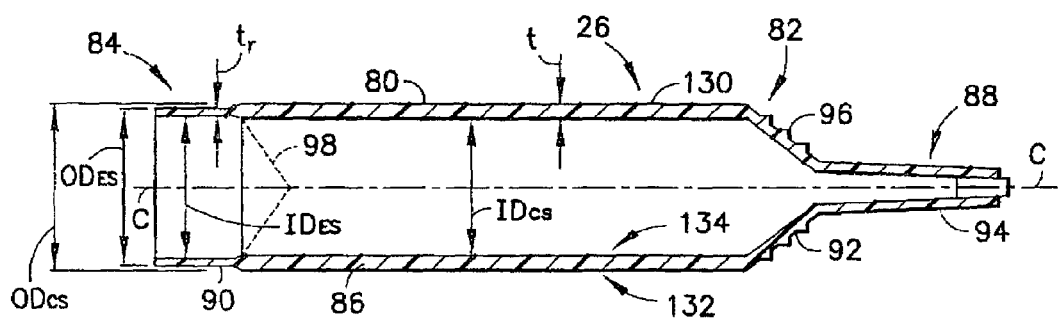
FIG. 14 is a cross sectional view taken along line 14-14 in FIG. 13.

FIGS. 3, 13, and 14 show a first embodiment of the syringe 26, which is specifically adapted to store a pre-positioned syringe plunger 98. Prior art syringes for medical fluid injection procedures are often stored with a pre-positioned syringe plunger. A difficulty with current disposable plastic syringes is that the syringes exhibit plastic creep over time and during sterilization heat cycles. This causes the plastic syringe to swell, particularly in the area of the pre-positioned syringe plunger. This often makes it difficult to load prior art plastic syringes into front-loading pressure jackets.

The syringe 26 shown in FIGS. 3, 13, and 14 overcomes this disadvantage by storing the syringe plunger 98 in an increased diameter expansion section 90 formed at the proximal end 84 of the syringe body 80. The expansion section 90 is formed proximally of the cylindrical main body 86 of the syringe body 80. At the expansion section 90, a wall 130 of the syringe body 80 narrows from a thickness t to a reduced wall thickness $t_r$. Thus, an inner diameter $ID_{es}$ of the expansion section 90 is larger than an inner diameter $ID_{cs}$ of the cylindrical center section or main body 86. The reduced wall thickness $t_r$ at the expansion section 90 allows the expansion section 90 to expand outward under the force exerted by the syringe plunger 98 without an outer diameter $OD_{es}$ of the expansion section 90 becoming larger than an outer diameter $OD_{cs}$ of the main body 86.

As shown in FIG. 14, both an outer surface 132 of the wall 130 of the syringe body 80 and an inner surface 134 of the wall 130 of the syringe body 80 taper to form the reduced wall thickness $t_r$ at the expansion section 90. In particular, the outer surface 132 of the wall 130 of the syringe body 80 may taper inward toward a central axis C of the syringe body 80 and the inner surface 134 of the wall 130 of the syringe body 80 may taper outward away from the central axis C of the syringe body 80 to form the reduced wall thickness tr. An alternative configuration to the foregoing is to only taper the inner surface 134 of the wall 130 of the syringe body 80 outward away from the central axis C of the syringe body 80.

The reduced wall thickness $t_r$ at the expansion section 90 of the syringe 26 accommodates the expansion and plastic creep of the plastic syringe body 80 even after long periods of storage. Even after long storage periods, the syringe 26 with pre-positioned syringe plunger 98 may be quickly and easily inserted into front-loading pressure jacket systems, such as the pressure jacket assemblies 30 shown in FIGS. 1 and 2. When the syringe 26 is inserted into the pressure jacket 32 and ready for use, the syringe plunger 98 is engaged by the injector drive piston 24 in the manner discussed previously and moved forward from the expansion section 90 to the center section or main body 86 of the syringe 26, which may be referred to as the "working zone" of the syringe 26.

Figure 15:
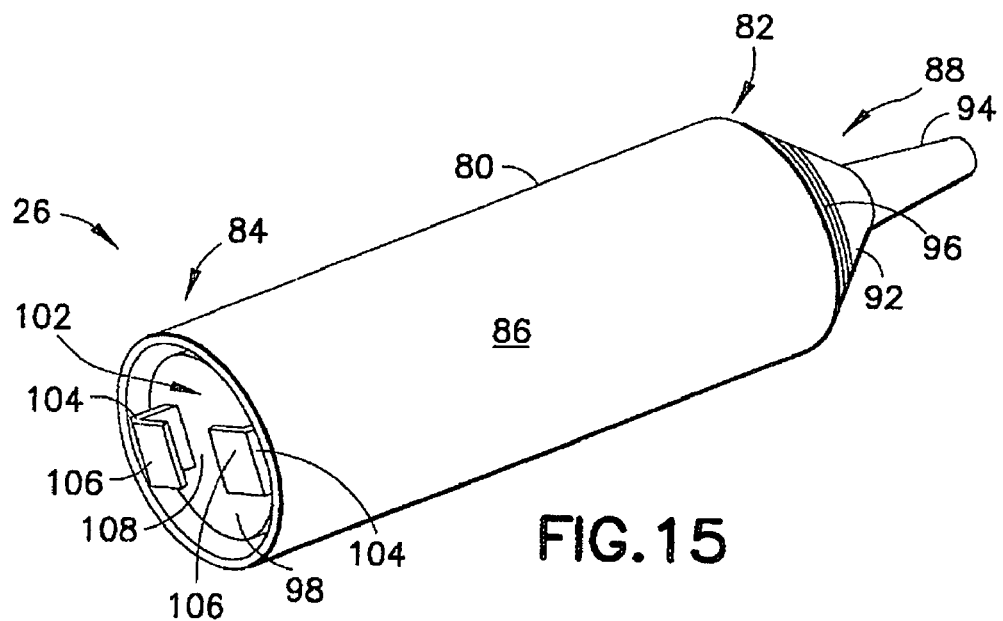
FIG. 15 is a perspective view of another embodiment of the syringe, which may be used in the fluid injection apparatus of the present invention.

FIG. 15 shows the syringe 26 according to another embodiment. The syringe 26 shown in FIG. 15 is substantially identical to the syringe 26 illustrated in FIGS. 3, 13 and 14, but does not have the increased inner diameter expansion section 90 for accommodating a pre-positioned syringe plunger 98. The syringe 26 depicted in FIG. 15 may be utilized in exactly the same manner as the syringe 26 shown in FIGS. 3, 13 and 14 and may include a pre-positioned syringe plunger 98.

Figure 16:
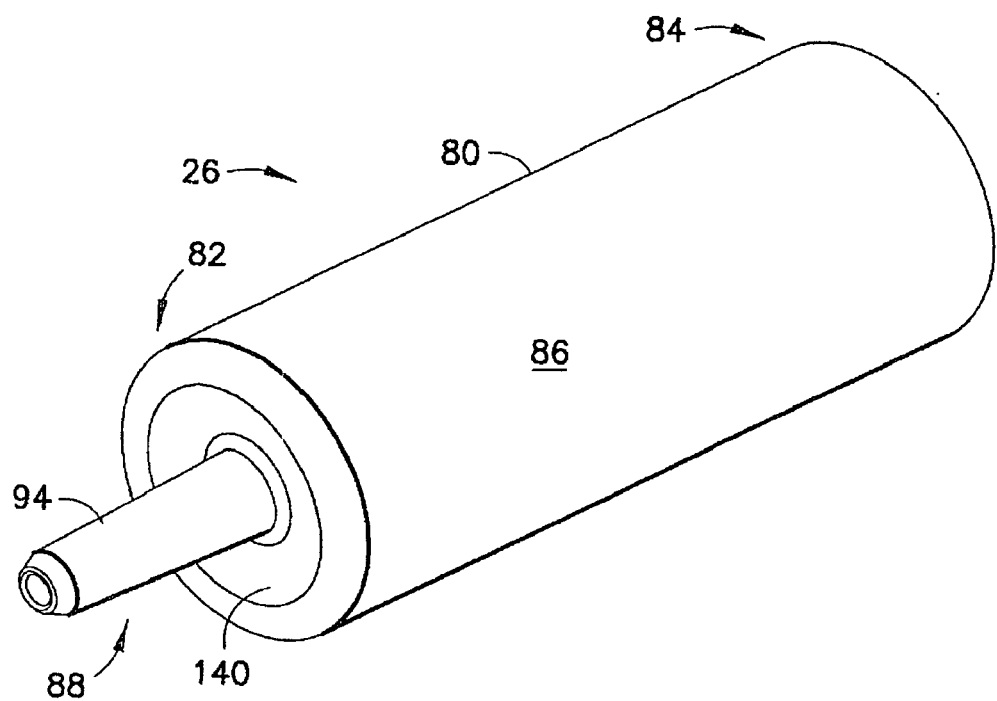
FIG. 16 is a perspective view a further embodiment of the syringe, which may be used in the fluid injection apparatus of the present invention.

FIGS. 16-18 show a still further embodiment of the syringe 26, which may be used with the fluid injection apparatus 10 and pressure jacket 32. The syringe 26, according to this embodiment, includes a concave shoulder 140 formed at one end of the main body 86 (i.e., at the distal end 82 of the syringe body 80). The elongated injection neck 94 of the injection section 88 extends outward directly from the concave shoulder 140. Thus, the syringe 26 of FIGS. 16-18 does not include a conical portion 92. The syringe 26 of FIGS. 16-18 may include an expansion section 90 (not shown in FIGS. 16-18) at the proximal end 84 of the syringe body 80.

Figure 19:
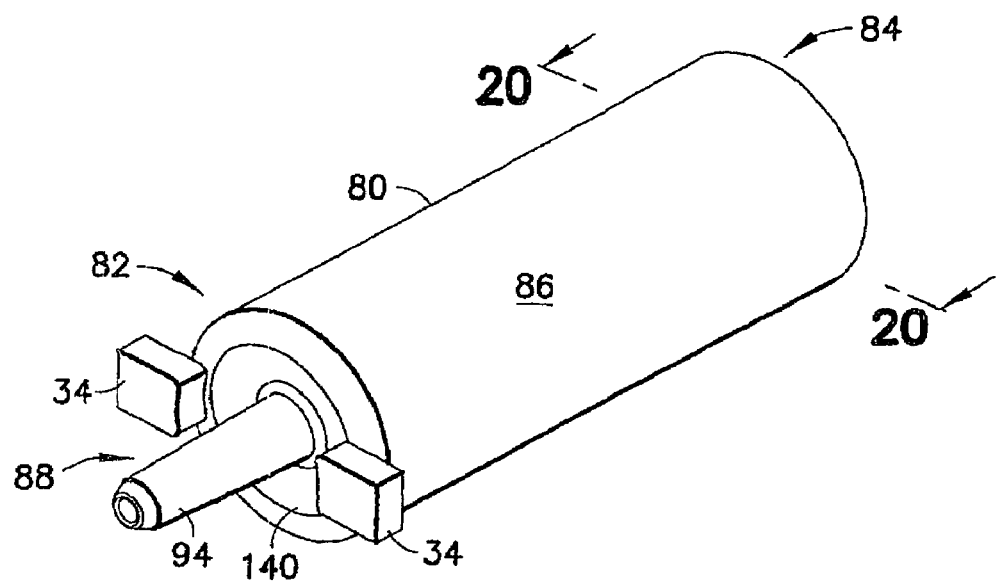
FIG. 19 is a schematic perspective view of the syringe of FIG. 16 shown coacting with modified locking members in accordance with the present invention.
Figure 20:
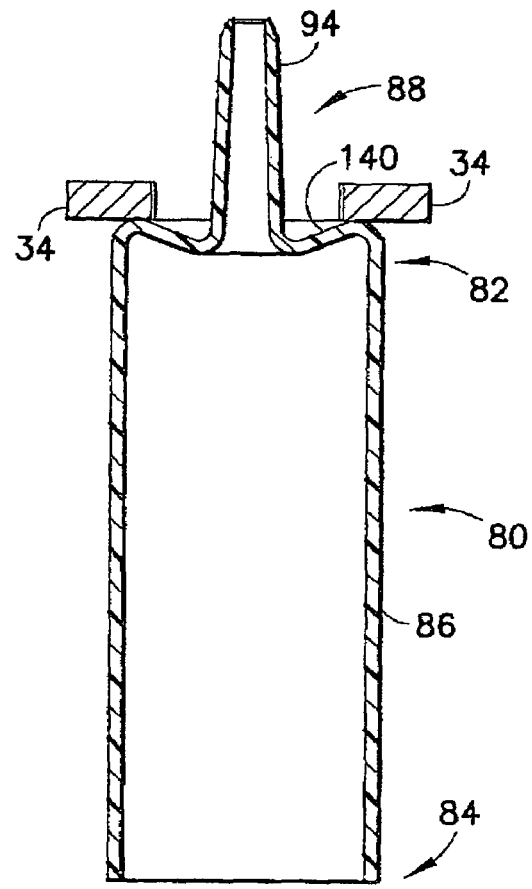
FIG. 20 is a cross sectional view taken along line 20-20 in FIG. 19.

The syringe 26 of FIGS. 16-18 allows modifications to the locking members 34, as illustrated in FIGS. 19 and 20. The locking members 34 no longer require grooves 122 for cooperating with the ridges 96 formed on the conical portion 92 of the previously described syringes 26. The locking members 34 may be substantially rectangular shaped for contacting the concave shoulder 140 formed on the syringe 26 of FIGS. 16-18. Thus, the syringe 26 of FIGS. 16-18 is maintained in the pressure jacket 32 during operation of the fluid injection apparatus 10 by contact between the conical shoulder 140 and the locking members 34. In particular, when the rectangular locking members 24 are moved from the disengaged position to the engaged position, the locking members 34 define the reduced diameter opening 128 (shown in FIG. 9) in the syringe receiving opening 42 in the pressure jacket 32. The reduced diameter opening 128 has a smaller diameter than the diameter of the concave shoulder 140. The contact between the concave shoulder 140 and locking members 34 will prevent the syringe 26 of FIGS. 16-18 from moving distally forward in the pressure jacket 32 during an injection procedure. The syringe 26 and locking fingers 34 interface is more robust than conical portion 92—locking fingers 34 interface described previously in this disclosure. Accordingly, only one or two locking fingers 34 may be necessary in accordance with this embodiment of the fluid injection apparatus 10 and pressure jacket 32. The interface between the syringe 26 and locking fingers 34, in this embodiment, does not require continuous contact around the circumference of the conical shoulder 140. Since only one or two locking fingers 34 may be necessary in this embodiment, an engagement mechanism with one or more "slidably" configured locking fingers 34 (not shown) may be used in place of the pivotal locking fingers 34 discussed previously.

While the present invention was described with reference to preferred embodiments of the fluid injection apparatus and syringe used therewith, modifications and alterations may be made to the present invention by those skilled in the art without departing from the scope and spirit of the invention. Accordingly, the foregoing detailed description is intended to be illustrative rather than restrictive. The invention is defined by the appended claims, and all changes to the invention that fall within the meaning and range of equivalency of the claims are to be embraced within their scope.

What is claimed is:

1. A pressure jacket for receiving therein a syringe comprising a cylindrical main body, a conical portion connected to the cylindrical main body, and a discharge outlet connected to the conical portion, the pressure jacket comprising:
   an elongated body having a proximal end configured to be removably associated with a fluid injection apparatus and a distal end comprising a radially outward extending flange;
   at least one locking member comprising a first end, having a radially outward extending projection, that is pivotally associated with the radially outward extending flange and a second end comprising a syringe engaging surface defining a curved groove adapted to engage a mating ridge formed on the conical portion of the syringe, the at least one locking member movable between an engaged position wherein the groove cooperates with the ridge formed on the conical portion of the syringe for preventing removal of the syringe from the elongated body and a disengaged position allowing insertion and removal of the syringe; and
   an actuation ring rotationally associated with the radially outward extending flange on the distal end of the elongated body and configured to move the at least one locking member between the engaged and disengaged positions, the actuation ring comprising at least one pair of tab members formed on an inner surface thereof and positioned on opposite sides of the radially outward extending projection of the first end of the at least one locking member such that rotational movement of the actuation ring causes the tab members to coact with the projection and move the at least one locking member between the engaged and disengaged positions.

2. The pressure jacket of claim 1, wherein a distal end wall of the actuation ring tapers inward toward a central axis of the body for guiding the syringe during insertion thereof into the body.

3. The pressure jacket of claim 1, wherein the at least one locking member comprises a plurality of locking members, the actuation ring configured to move the locking members between the engaged and disengaged positions.

4. The pressure jacket of claim 3, wherein the locking members are regularly spaced around the distal end of the body.

5. The pressure jacket of claim 1, wherein a distal end of the elongated body defines a syringe receiving opening for receiving the syringe and the proximal end of the elongated body is configured for removable association with the fluid injection apparatus.

6. The pressure jacket of claim 1, wherein the elongated body is made of substantially clear plastic.

7. The pressure jacket of claim 1, wherein the at least one locking member is pivotal in a plane substantially normal to the longitudinal of the pressure jacket.

8. A pressure jacket for receiving therein a syringe comprising a cylindrical main body, a conical portion connected to the cylindrical main body, and a discharge outlet connected to the conical portion, the pressure jacket comprising;
   an elongated body having a proximal end configured to be removably associated with a fluid injection apparatus and a distal end comprising a radially outward extending flange and defining a syringe receiving opening for receiving the syringe;
   at least one locking member comprising a first end, having a radially outward extending projection, that is pivotally associated with the radially outward extending flange and a second end comprising a syringe engaging surface defining a curved groove adapted to engage a mating ridge formed on the conical portion of the syringe, the at least one locking member movable between a disengaged position allowing the syringe to be inserted into the elongated body and removed therefrom through the syringe receiving opening and an engaged position wherein the at least one locking member defines a reduced diameter opening in the syringe receiving opening preventing insertion into and removal of the syringe through the syringe receiving opening; and
   an actuation ring rotationally associated with the radially outward extending flange on the distal end of the elongated body and configured to move the at least one locking member between the engaged and disengaged positions, the actuation ring comprising at least one pair of tab members formed on an inner surface thereof and positioned on opposite sides of the radially outward extending projection of the first end of the at least one locking member such that rotational movement of the actuation ring causes the tab members to coact with the projection and move the at least one locking member between the engaged and disengaged positions.

9. The pressure jacket of claim 8, wherein a distal end wall of the actuation ring tapers inward toward a central axis of the pressure jacket for guiding the syringe during insertion thereof into the pressure jacket.

10. The pressure jacket of claim 8, wherein the at least one locking member comprises a plurality of locking members, the actuation ring configured to move the locking members between the disengaged and engaged positions.

11. The pressure jacket of claim 10, wherein the locking members are regularly spaced around the distal end of the body.

12. The pressure jacket of claim 8, wherein the at least one locking member is pivotal in a plane substantially normal to the longitudinal axis of the pressure jacket.

* * * * *

UNITED STATES PATENT AND TRADEMARK OFFICE
CERTIFICATE OF CORRECTION

PATENT NO. : 7,361,156 B2 Page 1 of 1
APPLICATION NO. : 10/326583
DATED : April 22, 2008
INVENTOR(S) : Joyce et al.

It is certified that error appears in the above-identified patent and that said Letters Patent is hereby corrected as shown below:

In Column 15, Line 45, in Claim 4, after "end of the" insert -- elongated --.

In Column 15, Line 56, in Claim 7, after "longitudinal" insert -- axis --.

In Column 16, Line 4, in Claim 8, delete "comprising;" and insert -- comprising: --, therefor.

In Column 16, Line 49, in Claim 11, after "end of the" insert -- elongated --.

Signed and Sealed this

Fifteenth Day of July, 2008

JON W. DUDAS
*Director of the United States Patent and Trademark Office*